United States Patent [19]
Abbott et al.

[11] Patent Number: 5,104,791
[45] Date of Patent: Apr. 14, 1992

[54] PARTICLE COUNTING NUCLEIC ACID HYBRIDIZATION ASSAYS

[75] Inventors: Scot D. Abbott; Richard C. Ebersole, both of Wilmington, Del.

[73] Assignee: E. I. Du Pont de Nemours and Company, Wilmington, Del.

[21] Appl. No.: 154,091

[22] Filed: Feb. 9, 1988

[51] Int. Cl.$^5$ .................. C12Q 1/68; G01N 33/566; C07H 15/12; C12N 15/00
[52] U.S. Cl. ........................... 435/6; 436/501; 536/26; 536/27; 935/77; 935/78
[58] Field of Search .............. 435/6; 436/501; 536/26, 536/27; 935/77, 78

[56] References Cited
U.S. PATENT DOCUMENTS
4,806,463  3/1989  Goodchild et al. .................. 435/5

FOREIGN PATENT DOCUMENTS
200113A2  11/1986  European Pat. Off.
2169403   7/1986   United Kingdom.
8705334   9/1987   World Int. Prop. O.

OTHER PUBLICATIONS
Walker et al., The Language of Biotechnology, pp. 21-22 and 35-36, American Chemical Society, 1988.

Primary Examiner—Robert A. Wax
Assistant Examiner—Mindy B. Fleisher
Attorney, Agent, or Firm—George A. Frank

[57] ABSTRACT

An improved nucleic acid hybridization assay, relying on particle counting, is provided. Presence and quantity of target nucleic acid is determined by detecting, upon hybridization, signals associated with particle aggregation or coincident signals from particles and reporters.

11 Claims, 4 Drawing Sheets

PARTICLE COUNTING NUCLEIC ACID HYBRIDIZATION ASSAYS

FIELD OF THE INVENTION

This invention relates to nucleic acid hybridization tests and more specifically a particle counting assay based particle aggregation.

BACKGROUND ART

Nucleic acid hybridization tests, also referred to as DNA or RNA probe tests provide new means of analyzing genetic information contained in test samples. Nucleic acid hybridization assays can thus provide important new clinical diagnostic capability and yield information on the genetic basis and susceptibility to disease. For example, hybridization assays have established relationships between viral infections and cancer. Prenatal diagnosis of genetic disease and detection of inherited disease traits have also been reported. Nucleic acid hybridization assays have also found application in the identification of slow growing and resistant infectious organisms [J. Skylar, Human Pathology, 16 (7), 654 (1985)].

Mixed-phase hybridization systems have typically been used to perform these assays. In mixed phase assays the hybridizations are performed on a solid phase such as nylon or nitrocellulose membranes. These assays can be cumbersome involving complicated, multistep procedures. For example, the assays usually involve loading a membrane with sample, denaturing the DNA to create single-stranded molecules, fixing the DNA or RNA to the membrane, and saturating the remaining membrane attachment sites with heterologous nucleic acids to prevent the probe reagent from adhering to the membrane in a nonspecific manner. All of these steps must be done before performing the actual hybridization. The conventional membrane based test procedures are time consuming (4-12 hours) and complex—requiring multiple reagent additions, wash procedures, and hands-on manipulations [see, for example, M. J. Gore, Clin. Chem. News, 12 (6), 1 (1986)].

Membrane-based hybridizations are not always directly useful for crude samples. The membranes are subject to clogging. Moreover, crude samples contain proteins, lipids, mucopolysaccharides, etc., which compete for binding sites on the membranes and, when fixed, reduce the binding capacity of the membrane and contribute to nonspecific binding of reporter reagents. These competing interactions cause unacceptable background and diminished test response. Furthermore, target DNA is found typically in minute quantities ($<10^{-15}M$) in most test samples, since only a few copies of target DNA are present in each cell. For these reasons, for clinical diagnostic applications, the nucleic acids in test samples must be at least partially purified and concentrated prior to testing.

To circumvent these drawbacks, several new hybridization techniques have been reported in the literature. A. R. Dunn et al. [Cell, 12, 23-36 (1977)] along with M. Ranki et al. [Gene. 21, 77-85 (1983)] describe the application of sandwich hybridization procedures for probe tests. Sandwich hybridization assays generally involve the use of two probe reagents. One probe is attached to a solid phase support such as a membrane and the other probe is attached to a label. Both probes are complementary to a portion of the target nucleic acid. When target nucleic acid is present, the labeled probe will be bound to the solid phase support through the target nucleic acid and can then be detected after washing the solid phase support. M. Ranki et al., Current Topics in Microbiology and Immunology, 104, 307-318 (1983), report that the sandwich hybridization assays can be performed on crude samples. The sandwich hybridization technology can use various solid supports and has provided a way to reduce sample pretreatment complexity and to reduce the number of assay steps.

Despite gains realized in enhanced procedural simplicity and reduced sample pretreatment, sandwich hybridization assays continue to suffer from long equilibration times. This is primarily caused by the concentration dependence of hybridization reactions which dictates that longer equilibration times are required at lower target DNA and probe reagent concentrations (B. D. Hames and D. J. Higgins, eds., Nucleic Acid Hybridizations, pp 48-53, IRL Press, 1985).

Sandwich hybridization assays depend on two independent hybridization events. The reaction times are influenced by both the reporter probe and capture probe concentrations. Furthermore, the reaction rates are known to be slower on solid phase reagents than in solution. In addition, the equilibration procedures and wash steps, required in the assay to free the solid phase supports from unhybridized probe, also extend testing time and thus diminish clinical usefulness of the technology. Currently, the long assay times prevent test results from being used in cases of emergency or performed in time to be used during a patient's office appointment.

The most severe drawback of current hybridization assays for both diagnostic and research applications, has been inadequate test sensitivity. Generally, only a few copies of target nucleic acid are present in test materials of clinical interest. For example, infectious disease specimens generally contain only a few infectious organisms. The presence of from $1-1 \times 10^6$ organisms is generally considered clinically important. Since each organism contains only a few copies of target nucleic acids per cell (4 to 100), the total target nucleic acid available ranges from approximately $10^{-16}$ to $10^{-22}$ moles. This is below the current limit of detection for hybridization assays. For this reason, hybridization assays have not been generally applicable to direct specimen testing but have found use in testing specimens in which the number of organisms has been increased by culturing.

Several methods which have recently been disclosed attempt to circumvent the constraint of limited copies of target nucleic acids. In a patent application, Ser. No. WO 84/02721, Kohne described the use of probes directed against RNA targets. Since many thousands of copies of target RNA can be produced in vivo during expression of a single copy of DNA, RNA probe tests would appear to be inherently more useful and thus applicable to direct specimen testing. However, RNA targets are particularly labile and subject to enzymatic digestion by the large quantities of ribonucleases found in samples.

K. B. Mullis and K. B. Mullis et al. U.S. Pat. No(s). 4,683,202 and 4,683,195, both issued July 28, 1987, respectively, disclose a gene amplification technique which can be used to multiply the number of DNA copies present in test samples. In this approach, the target DNA is replicated multiple times in vitro using a DNA polymerase enzyme. This way, the number of copies of DNA can be greatly increased (about $10^6$-fold). Once amplified, the target DNA can then be tested using conventional hybridization assays. This technique, known as a polymerase chain reaction procedure, involves multiple steps which add time additional user manipulations and reagent costs to the overall hybridization assay.

Attempts to modify the original sandwich hybridization assay principle also have not afforded the required sensitivity. For example, in European Patent Application 154,505, J. E. Monahan et al. describe a sandwich hybridization format specifically designed to detect a specific single nucleotide change in the nucleotide sequence such as would occur as a result of a genetic mutation. During analysis, the target DNA is contacted with restriction endonucleases specifically selected to cleave or, alternatively, to conserve the integrity of the strand at the point of sequence change. Since the integrity of the target chain depends on the presence or absence of the nucleotide sequence change site, the integrity of the target chain is detected by determining whether the reporter probe remains attached to the solid phase immobilized capture probe during hybridization or is present in the solution following separation of the two phases. Alternatively, if detection depends on agglutination, settling rates or changes in agglutination could be used to signal the integrity of the target chain after treatment with restriction enzymes.

In European Patent Application 130,515 A2, Dattagupta et al, describe a dual hybridization assay concept for detecting nucleotide sequences in DNA samples. This approach is similar to that of Monahan et al. in that both make use of first and second nucleic acid probes, one of which is attached to a solid phase support complementary to adjacent sequences at a specific restriction site which is unique to the target DNA. The method is ideally suited to the detection of inherited diseases such as sickle cell anemia or to detect point mutations occurring in known gene sequences. However, both approaches suffer from inherent drawbacks. Both of these methods are limited in scope of application since probe reagents must be prepared complementary to sequences adjacent to a restriction site. Sequences distant from the restriction site cannot be used since the same enzyme can produce multiple cuts in large pieces of DNA. Applications of these assays are further limited in scope to gene sequences for which restriction enzymes are available. Furthermore, these assays are not suited for quantitative analysis. The absence of target DNA would appear as if restriction sensitive target were present since the partitioning of the solid phase probe would result in solubilized labeled probe.

While the techniques of Monahan et al, and Dattagupta et al. did achieve increased specificity, they did not achieve the desired increase in sensitivity. Furthermore, they do not suggest ways for enhancing detection of these labels. Neither the method of Monahan et al. nor of Dattagupta et al. extends the detection limits of sandwich hybridization assays.

Patent Application WO 86/03782 describes a sandwich hybridization assay having high sensitivity. One of the reagents utilized is a polynucleotide covalently bonded to a solid resin particle or bead. The second reagent is a labeled restriction enzyme fragment of the normal gene sequence but complementary to a different portion of the target gene, the target binding sites of the two reagents being separated by a restriction enzyme cleavage site. In performing the assay, the sample polynucleotide to be tested is first treated with the specific restriction enzyme and the resulting digest brought into contact with the two reagents under hybridization conditions. Following the hybridization step, the materials bound to the solid phase reagent are separated and washed free of the remaining unbound labeled reagent. The presence of any label bound to the solid support is then determined. While this method affords relatively high sensitivity, the method is complicated by the required wash steps.

Abbott et al. U.S. Pat. No. 4,521,521, issued June 4, 1985, describes a highly sensitive and rapid method for quantitatively assaying analytes in liquid media by directly measuring changes in particle size distribution of reagent particles having analyte insolubilized thereon in a system undergoing antibody-induced aggregation.

There exists a continuing need for a nucleic acid hybridization assay which is highly specific, has enhanced detection sensitivity and is rapid and easy to perform.

SUMMARY OF THE INVENTION

The particle counting nucleic acid hybridization assay of this invention comprises the steps of:
(a) contacting a sample suspected of containing target nucleic acid with capture probe and reporter probe wherein
(i) the capture probe is a particle-bound nucleic acid complementary to and capable of hybridizing with at least a portion of the target nucleic acid and consists essentially of a capture particle having a particle diameter range of 0.01–15 μ and a capture nucleic acid; and
(ii) the reporter probe consists essentially of a reporter nucleic acid complementary to and capable of hybridizing with at least a portion of the target nucleic acid and a reporter moiety;
wherein the capture nucleic acid and the reporter nucleic acid are
(A) complementary to separate portions of the target nucleic acid;
(B) complementary to distinct portions of the target nucleic acid unless said target nucleic acid contains at least two segments of identical nucleotide sequence of suitable specificity; and
(C) not complementary to each other;
(b) determining the presence and/or quantity of target nucleic acid by detecting signals associated with particle aggregation in the event the reporter moiety is a particle or coincident signals of particle detection and reporter detection in the event the reported is not a particle.

DESCRIPTION OF THE INVENTION

For the sake of convenience and ready reference, the following definitions will be used in describing the instant invention. Nucleic acid includes single-stranded deoxyribonucleic acid (DNA), ribonucleic acid (RNA) and arabinonucleic acid (ANA). Target nucleic acid is the nucleic acid which is being tested for in a sample; the testing being carried out on the denatured, single-stranded form. Capture probe is a particle-bound nucleic acid, complementary to and capable of hybridizing with at least a portion of the target nucleic acid and is made up of a capture particle and a capture nucleic acid. Reporter probe is a nucleic acid which is complementary to and capable of hybridizing with a separate and distinct portion of the target nucleic acid and has a reporter moiety (particle, chromophore, fluorophore. etc.) bound to it.

The particle counting nucleic acid probe assay of this invention depends for its enhanced detection sensitivity on the utilization of special reporter moieties which, given the format of the assay, permit either the sensitive measurement of particle size distribution or of coincident signals as a measure of the amount of target nucleic acid present.

Figure 1:
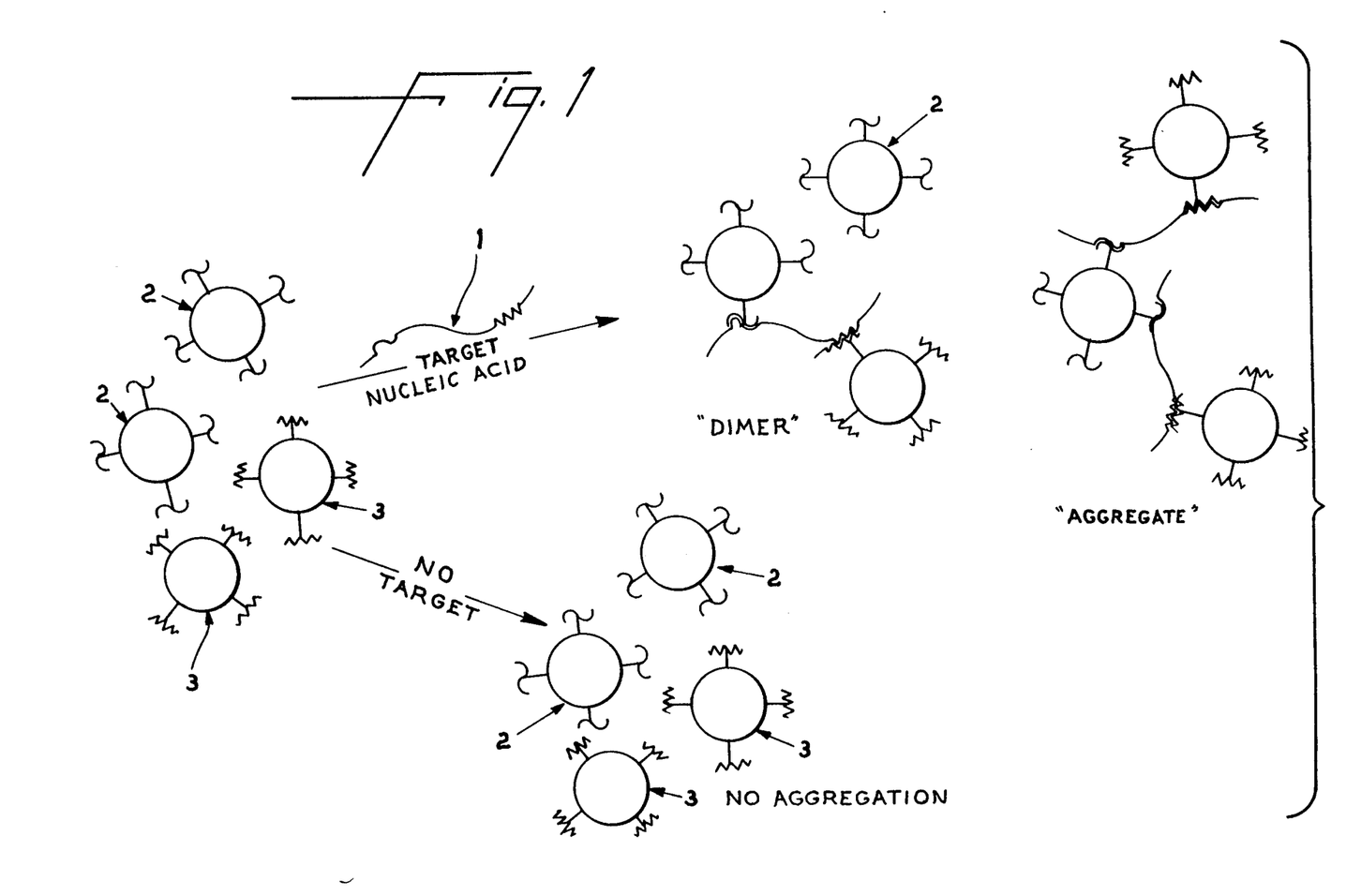
FIG. 1 is a schematic representation of a particle counting hybridization assay based on aggregation.

One possible format or configuration of the particle counting probe assay relies on particle aggregation. In this assay, shown schematically in FIG. 1, target nucleic acid 1 will hybridize with a capture probe 2 and a reporter probe 3 which contains a particle as the reporter moiety. In the presence of target nucleic acid the capture and reporter probes can bind to the target nucleic acid leading to the formation of dimer, trimer or higher aggregates of the capture and reporter probes with the target nucleic acid. In the absence of target nucleic acid, no aggregation occurs. The differences in the particle size distributions found in such an assay and one carried out in the presence of known amounts of target nucleic acid can then be used to determine the amount of target nucleic acid present in the sample.

Figure 2:
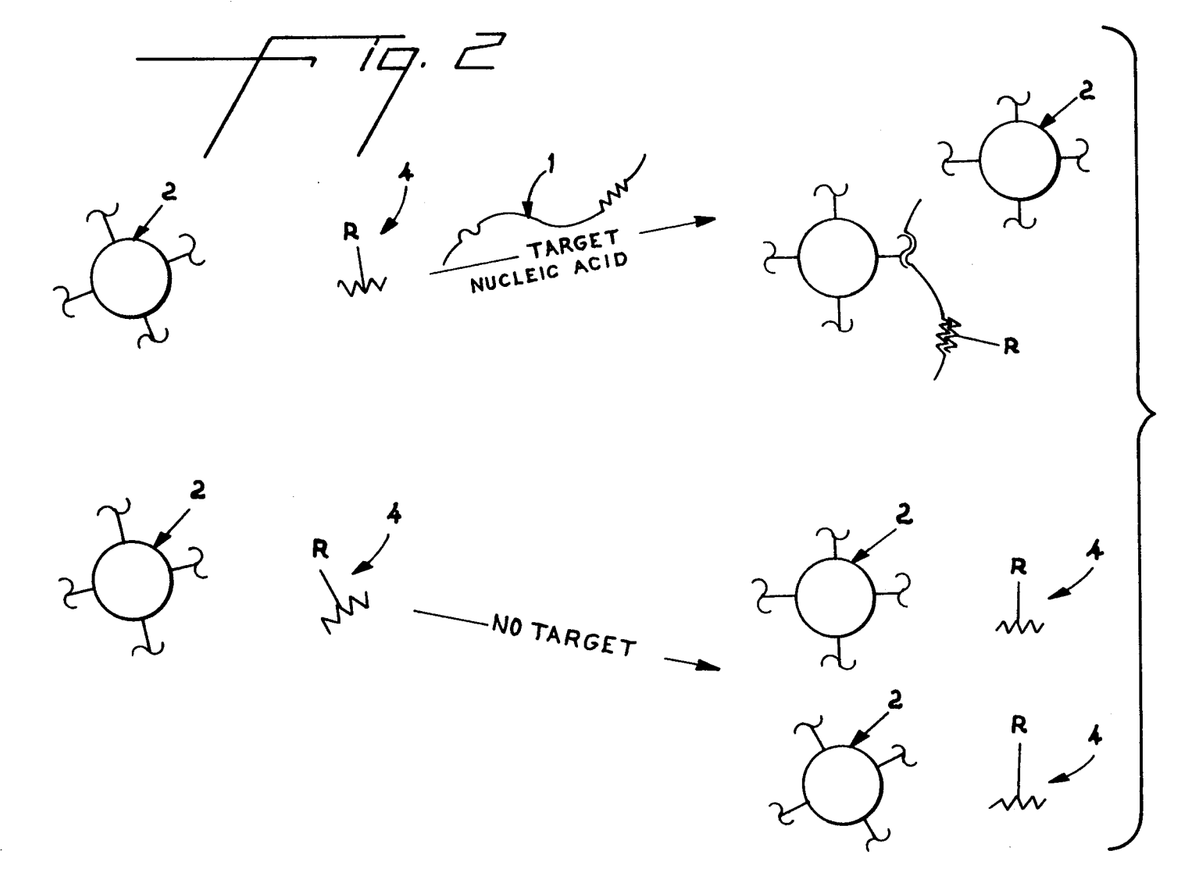
FIG. 2 is a schematic representation counting hybridization assay based on signal coincidence.

Another configuration of the particle counting probe assay of this invention relies on signal coincidence. In this assay, shown schematically in FIG. 2, target nucleic acid 1 will hybridize with a capture probe 2 and a reporter probe 4 which contains a reporter moiety which is detectable by means other than particle counting. The capture probe and the reporter probe can both bind to the target nucleic acid to form a complex linked through the target nucleic acid. When this complex passes through a detector that can simultaneously count particles and detect a reporter moiety, a signal can be generated when a particle and reporter moiety are detected coincident with one another. The number of coincident events for a sample can be related to the amount of target nucleic acid present. Unreacted particles and reporter moieties, although individually detected, do not give rise to coincident signals.

Generally, one must consider several performance requirements for a useful probe assay. The assay procedure should be sufficiently simple to be performed manually or easily automated. The procedure should involve as few physically separate steps such as washing and timed reagent additions as possible, and should utilize minimum amounts of expensive and rare reagents. Tolerance to dilution and manipulation errors during the procedure are also important. It is highly desirable that assay reagents and procedures be common to several assays in order to permit detection of a variety of target nucleic acids with a minimum of alterations in reagent(s) and assay conditions. Such assay procedures, in turn, can be adapted for use on automated analyzers. Additionally assay results should be available in minutes, rather than hours or days for example to permit in-office diagnosis of patients. Most importantly, an assay must provide an acceptable level of sensitivity and specificity for the specific target nucleic acid being tested, while the dynamic range of the assay should correspond to the range of target nucleic acid concentration found in typical samples.

Factors to be considered and tailored in preparing the reagents necessary to carry out the particle counting nucleic acid hybridization assays of the instant invention include the nature of the capture particle, the capture nucleic acid, the reporter, and the reporter nucleic acid and the chemistries used to link the capture particle and reporter moiety to the capture nucleic acid and reporter nucleic acid, respectively.

The capture and reporter nucleic acids useful in the instant invention must have sequences that are complementary to separate and, usually, distinct portions of the target nucleic acid which are unique to the target nucleic acid. In general, the capture and reporter nucleic acids should contain as many nucleotides as necessary to define the unique complementary sequence of the target nucleic acid but not be longer than necessary. The addition of nucleotides which are not essential to impart specificity to the capture and reporter nucleic acids can provide sites for nonspecific hybridization and can reduce the reactivity of the solid phase reagents. Also, longer capture and reporter nucleic acids require longer hybridization times during the assay. It is generally accepted that the preferred number of nucleotides needed to impart acceptable specificity in a probe is about 18 to 200.

It is essential that the capture and reporter nucleic acid sequences be complementary to separate sections of the target nucleic acid. If capture and reporter nucleic acids were to be complementary to the same section of the target nucleic acid, hybridization of one of the probes (capture or reporter) with the target nucleic acid would block hybridization of the other with the target nucleic acid and would thus prevent meaningful signal generation in particle counting assays of this invention.

Although customarily complementarity to distinct sections of the target nucleic acid is desired by the capture and reporter nucleic acids, this is not essential when the target nucleic acid contains at least two copies of a nucleotide sequence which is of suitable specificity for use as a complementary sequence. When this occurs, the capture and reporter nucleotide sequences can be the same. In the particle aggregation format, this would mean that the capture probe and the reporter probe can be the same. In contrast, when signal coincidence is relied on for detection, having repeating nucleotide sequences as the targets within the target nucleic acid can lead to undesirable results since the possibility exists for a target nucleic acid to have only capture probes or only reporter probes hybridized to it.

The distance between complementary sequences on the target nucleic acid for the capture nucleic acid and reporter nucleic acids is also an important consideration in selecting the nucleotide sequences of the capture and reporter nucleic acids. The distance between the capture and reporter binding sites on the target nucleic acid should be large enough to allow good hybridization of both the capture and reporter probes without steric hindrance. Capture and reporter binding sites separated by at least 50 nucleotides are generally suitable for application of the instant invention. Target nucleic acids with capture and reporter sequences which are separated by less than 50 nucleotides can be useful but, in that case, the size of the particles used in the capture and/or reporter probes need to be optimized for these shorter distances. The smaller particles necessary for smaller separation distances, however, can reduce the sensitivity of the detection system. In general, separation distances of less than 10 nucleotides are too small for useful application of the instant invention.

Yet another consideration on selecting appropriate capture and reporter nucleic acids is the need to assure that the capture and reporter sequences are not complementary to each other. Excessive complementarity will cause hybridization of the capture and reporter probes to each other and result in ambiguous assay results.

Nucleic acids useful as capture and reporter nucleic acids in carrying out the particle counting nucleic acid hybridization assays of this invention can be obtained by purification from natural sources, through biosynthetic procedures using known cloning techniques [see e.g., T. Maniatis et al., Editors, "Molecular Cloning Laboratory Manual", Cold Spring Harbor, 1986] or synthetically using manual or automated nucleic acid synthesis techniques. Nucleic acids containing approximately 60 nucleotides or less are most readily prepared using automated nucleic acid synthesizers while cloning techniques can be used to produce nucleic acids of up to approximately 25,000 nucleotides.

Nucleic acids used as capture and reporter nucleic acids should be substantially pure for best results in hybridization assays. Nucleic acids produced synthetically often contain impurities called failure sequences which result from less than 100% reaction efficiency of the nucleotide coupling reactions. Use of probe reagents made from nucleic acids containing failure sequences can compromise both the specificity and sensitivity of the assay. Specificity is reduced because failure sequences which have incomplete chains increase the likelihood of nonspecific hybridization (since target selection is based on fewer nucleotides). Sensitivity is reduced since nucleic acids with one or more nucleotide deletions are no longer complementary to the target nucleic acid.

While nucleic acids obtained from biosynthetic and natural sources can be used as capture and reporter nucleic acids, the synthetic nucleic acids are preferred. The synthetic nucleic acids can be made with nucleotides which have been chemically modified to attach linker arms permitting the incorporation of linker arms in predetermined positions in the nucleic acid. This, in turn, permits the attachment of a capture particle or reporter moiety to the nucleic acid [J. L. Ruth et al., DNA, 4, 93 (1985)].

A variety of methods can be used to link a nucleic acid to a capture particle or reporter moiety. This linking can take place prior to the hybridization reactions or afterwards. Linking agents of the hetero- and homobifunctional types including glutaraldehyde N,N'-o-phenylenedimaleimide N,N'-oxydimethylenedimaleimide, N-succinimidyl 4-(N-maleimidomethyl)cyclohexane-1-carboxylate, N-succinimidyl m-maleimidobenzoate, N-succinimidyl 3-(2-pyridyldithio)propionate, methyl 3-(4-dithiopyridyl)propionimidate and N-succinimidyl iodoacetate can be utilized. The linking agents can contain spacer segments of various length to permit optimization of nucleic acid attachment. Noncovalent bonding of the reporters or particles to nucleic acid can also be useful, such as the use of various ligands and binders attached to nucleic acids and the reporters, biotinylated nucleic acids and avidin-particle or avidin-reporter moiety conjugates and arabinonucleic acid and anti-arabinose antibody-particle conjugates. (Labeled anti-arabinose antibodies for the detection of ANA have been described in applicants' assignee's copending U.S. patent application, Ser. No. 812,574, filed Dec. 23, 1985).

It has been found that linking techniques producing noncharged hydrophilic linker groups are preferred in the assays of this invention. Such linkages minimize nonspecific binding resulting from hydrophobic and/or ionic interactions with sample nucleic acids and competing proteins.

The length of the linker arm can be an important factor in providing appropriate reactivity of the capture particles or reporter moieties on the nucleic acids prior to hybridization. Linker arms which are too short can reduce hybridization efficiency due to steric hindrance of the capture particle or reporter moiety with the target nucleic acid while linker arms which are too long can reduce hybridization efficiency possibly because the nucleic acid folds back onto the capture particle or reporter moiety.

In cases where the capture particles or reporter moieties are not suitable for direct coupling to the capture or reporter nucleic acid, the nucleic acid can be attached to a carrier molecule such as a polymer.

Particles useful as the capture particles or reporter particles can be selected primarily on the basis of detectability of their properties such as light refraction, electrical reactance and particle size. Additional selection criteria include surface properties necessary for immobilization on nucleic acids.

Generally, particles have a diameter range of 0.01 to 10 microns, and up to approximately 15–20 $\mu$, with the range of 0.02 to 0.5 microns being preferred. In this size range, the particles have a favorable balance of properties including the advantage of a high surface area to volume ratio. This permits increased surface coverage of the particle with the capture or reporter nucleic acid. Furthermore, particles in this size range are readily maintained as stable dispersions or emulsions by the use of surfactants and protein stabilizers and appropriate buffering conditions. Also it is believed advantageous to provide particles which are relatively small so that the diffusion rates and, therefore, reaction rates are as high as possible. Furthermore, while uniform size particles are preferred, the particles do not need to be homogeneous in size.

Among many particles useful in the instant invention, certain shell-core polymeric particles are described in U.S. Pat. No(s). 4,401,765, 4,480 042, and 4,703,018, all incorporated herein by reference. The particles do not have to be solid, stable liquid droplet emulsions can also be useful in preparing the reagents of the instant invention. Materials useful for making particles include metals such as metal sols, metal oxides, synthetic homo- and copolymers such as polystyrenes, crosslinked polystyrenes, acrylamides, methacrylates, soluble polymers such as chitin, and dextrans, and polymers rendered insoluble by crosslinking.

In carrying out the assays of this invention, careful considerations need to be given to assay conditions. In general, since hybridization rates depend on the random collisions between the complementary nucleic acid strands, conditions influencing that rate, the effectiveness of the collisions, and the stability of the resulting duplex, such as concentration of the capture and reporter probes, temperature, and assay milieu, have to be chosen with care.

It is desirable to carry out the assays of this invention using capture and reporter probe particle concentrations in the range of approximately $10^4$–$10^9$ particles/mL. While high probe concentrations can increase the rate of hybridization, they can reduce the accuracy of determining the particle size distribution in the detection phase. In some instances, therefore, a compromise between reduced hybridization rate and increased accuracy of particle counting needs to be achieved. Alternatively the accuracy of the particle counting process can be enhanced by diluting the reaction mixture after hybridization has occurred but prior to particle counting. During the dilution and subsequent measurement steps, it is important not to alter the particle size distribution by dissociation of the aggregates or by nonspecific aggregation of the remaining probes. Dissociation of the aggregates can be minimized by maintaining high salt concentration (0.5–1.5 M $Na^+$) in the diluent. Nonspecific aggregation can be minimized by using surfactants in the reaction mixture and diluent.

Hybridization reactions are temperature dependent because the melt temperature of the duplex strands vary with nucleotide composition and strand length. For this reason, there is an optimum temperature for each assay. In general, a temperature approximately 25° C. below the lowest melt temperature (capture and reporter to target) can be utilized.

Salt ($Na^+$) concentration can affect the rate of hybridization and, therefore optimum salt concentration can vary for different assays. Generally, sodium ion concentrations in the range of 0.3 to 1.5 M provide acceptable rates of hybridization, while sodium ion concentrations below 0.1 M often lead to significantly slower rates. Divalent cations which can be found as impurities in many reagents can also lower hybridization rates. To avoid this, it may be necessary to include a chelator such as EDTA in the assay milieu.

When the assay of the instant invention is carried out utilizing a signal coincidence detection format, reporter moieties other than particles are preferred. These reporters must be detectable in a way different from the detection of the particles of the capture probe. The reporter groups include fluorescent, absorbent, radioactive electrical reactance and luminescent moieties.

Instrumentation useful in carrying out the assay of this invention depends primarily upon the type of capture probe and reporter moiety being used. When both the capture probe and reporter probe contain particles, as in the particle aggregation format, then a detection system capable of measuring changes in particle size needs to be used. There are many ways to detect changes in particle size such as by photometry, measuring angular dissymmetry and electrical reactance, and by optical zone particle counting. This latter technique, which is preferred, can examine individual particles and determine particle concentrations of a given size in a mixture. Under favorable conditions, this technique can detect as few as 1 particle of a given size in a sample containing as many as $10^{10}$ particles.

When signal coincidence detection is utilized, for example, when the reporter probe contains a fluorescent moiety, the simultaneous occurrence of a particle detection signal, such as light scatter, and a fluorescent signal from the hybridized complex, when excited by actinic radiation, is detected. This simultaneity indicates that the complex contains both capture particles, which cause light scatter, and a fluorescent moiety, which causes fluorescence. Any conventional coincidence detector can be used for this purpose such as a detection device similar to that used in a fluorescent cell sorter. Upon completion of an assay, with such device only the target nucleic acids which have both capture particles and reporter moieties attached would yield a signal. Reagents which are not hybridized to a target nucleic acid would either fluoresce or scatter light, but not both.

Using either the particle aggregation or signal coincidence formats it is feasible to assay for multiple target nucleic acids present in a single test sample. For example, using the particle aggregation mode, capture probes and reporter probes can be prepared for two separate target nucleic acids using detectably different particle sizes for the particles of the different sets of probe reagents. Aggregation of each different size particle can then be monitored independently and thereby determine the presence and concentration of each target nucleic acid.

Using the signal coincidence format, different reporter probes can be prepared which, for example, contain fluorescent moieties which fluoresce at detectably different wavelengths. Coincidence frequency for each reporter/capture pair can then be monitored to determine the concentration of each target nucleic acid.

The following example illustrates a particle counting hybridization assay for the detection of HIV nucleic acid utilizing particle aggregation detection.

EXAMPLE

HIV Assay

A. Preparation of Nucleic Acids

Three nucleic acid reagents were required for assaying HIV nucleic acid. The capture and reporter nucleic acids were synthesized with nucleotide sequences complementary to separate and distinct regions of the HIV gene. They were prepared using an Applied Biosystems Inc, model 380B DNA synthesizer using standard phosphoramidite coupling chemistry. In each of the capture and reporter nucleic acids, one of the thymidine residues in the sequence was replaced with a thymidine derivative substituted with a linker arm at the C5 position as described by Ruth et al., [DNA 4, 93 (1985)]. This substitution provided the sites for linking the capture particle and reporter moiety to the nucleic acid. The nucleotide sequence for each probe oligomer is listed below, with an asterisk indicating the position of the modified thymidine:

Reporter nucleic acid:
5'-dCTTCCCTTGTAGGAAGGCCAGATC-3'
                *

Capture nucleic acid:
5'-dTGGTGGGGCTGTTGGCTCTGGTCTGCTCTGAAGAAA-3'
                *

Complementary regions of the HIV gene are shown below
with each of the two probe nucleic acids:
Sequence
2051 AAATGAAAGATTGTACTGAGAGACAGGCTAATTTTTTAGGGAAGATCTGGCCTTCCTACAAGGGAAGGCCAGGAAT
                                              3'-CTAGACCGGAAGGATGTTCCCTTC-5'
                                                                    |
                                                                 particle Sequence
2118 CAGGGAATTTTCTTCAGAGCAGACCAGAGCCAACAGCCCCACCATTTCTTCAGAGCAGACCAGAGCCAACAGCCCCACCAG
                                              3'-AAAGAAGTCTCTGCTGGTCTCGGTTGTCGGGGTGGT-5'
                                                                    |
                                                                 particle HIV target nucleic acid was prepared by the method of Hahn et al., Nature, 302, 166 (1984). The lambda phage containing the 9.1 kilobase BH10 restriction insert of the HIV genome was obtained from the National Institutes of Health. The phage was cultured in *E. coli* and harvested. The phage DNA was then purified using standard techniques. The entire 50 kilobase (phage plus HIV) nucleic acid was then used as the target nucleic acid.

B. Preparation of Capture and Reporter Probes

The capture probe was prepared by linking the capture nucleic acid to amino-derivatized polystyrene microspheres (a polystyrene core polymer having cross-linked polystyrene shell with pendant amino groups, average diameter of 0.8 $\mu$; obtained from pandex Inc.) using isocyanate activation.

A 0.5 g quantity of the microspheres was added to a solution of 2 mL of 1,6-diisocyanatohexane in 5 mL of anhydrous dioxane and the mixture was agitated overnight on a rotator. The resulting particles were centrifuged and washed several times with anhydrous dioxane to remove any unreacted isocyanate reagent. The particles were then reacted for several hours with 2.65 g of 1,6-diaminohexane in 7.0 mL of anhydrous dioxane. These particles were then washed with dioxane containing 5% (v/v) triethylamine, followed by washing with purified water. The particles were next reacted with 1 g of glutaric anhydride and 1.4 mL of 1-methylimidazole in 5.0 mL of water for 3 hours at room temperature. This last step was repeated and the particles were washed free of reagents using purified water. The particles were then washed twice with 25 mL of 50% (v/v) methanol-water, followed by two washings with 25 mL of methanol and finally two washings with 25 mL of anhydrous ethylether. The particles were then dried under vacuum over phosphorous pentoxide and sodium hydroxide.

The particles prepared above were then activated for linking to the capture nucleic acid by reacting 0.1 g of the particles with 0.1 g of carbonyldiimidazole in 1.5 mL of 3:2 dimethylsulfoxide:acetonitrile for 4 hours. The particles were then washed 4 times with 15 mL of the dimethylsulfoxide/acetonitrile solution.

Capture nucleic acid, 45 nanomoles in 1.4 mL of 100 mM sodium carbonate buffer (pH 9.0), was added to 100 mg of the activated particles prepared above. The reaction mixture was agitated on a rotator for 9 hours at room temperature. The resulting capture probe was washed twice in sequence with 1 M NaCl, 0.5 M NaCl, 30% methanol/water. 0.5% sodium dodecyl sulfate in 1.0 M NaCl, water, and 50% methanol/water.

A reporter probe was prepared as follows. 50 $\mu$L of an aqueous suspension (5% w/v) of polystyrene-polyvinylnaphthalene-polychloromethyl-styrene core-shell microspheres (0.5 $\mu$, prepared by a modification of the procedure described in Example 1 of U.S. Pat. No. 4,703,018, incorporated herein by reference; the modification relating to extending the growth stage of the core polymerization process with vinylnaphthalene in two stages to afford a core particle size of 0.5 ) was incubated with 23 ng of the reporter nucleic acid. After 68 hours at 4° C. the derivatized microspheres were centrifuged and washed three times with deionized water.

C. Assay Diluents

Prior to preparation of test reagents, all liquids were filtered through a 0.2-micron filter The following were prepared for subsequent use:

denaturing solution—0.1 N NaOH;

neutralization buffer—0.5 M $NaH_2PO_4$, containing 0.1% SDS detergent, adjusted to pH 7.5;

SSC—NaCl (8.76 g) and sodium citrate (4.41 g) dissolved in 400 mL water; pH adjusted to 7.0 with NaOH; final volume adjusted to 500 mL;

salmon sperm DNA blocking solution—salmon sperm DNA (Sigma Type-III sodium salt) dissolved in deionized water, final concentration of 10 mg/mL. DNA was sheared by passing it through an 18-gauge hypodermic needle, boiled for 10 min., and then stored at −20° C.

D. Assay Detection Apparatus

Samples of assay reaction mixtures were pumped by a syringe pump (Sage Instrument Co.) through an optical module (Abbott et al., U.S. Pat. No. 4,565,448, issued Jan. 21, 1986, incorporated herein by reference). This module produced an electrical signal consisting of a series of pulses of varying number and voltage which resulted from the passage of particles of varying size and number concentration through the module. The electrical signal was digitized, placed on disc by an a/d storage converter (Nicolet model 2090 series storage oscilloscope equipped with disc storage and IEEE 488 interface options). The signal was transmitted to a computer (Digital Equipment Corp. MINC model equipped with a VT125 graphics terminal) which tracked the signal, detected peaks and gathered the distribution of peak voltages, their time integrals and durations of peaks.

E. Qualitative Assay for HIV DNA

Negative control samples containing no target HIV DNA were prepared by mixing 1 $\mu$L of the salmon sperm stock solution (10 g) with 100 $\mu$L of 0.1 N NaOH. The solution was then heated in a 50° C. water bath for 3 min, to denature the DNA. Chilled neutralization buffer (900 $\mu$L) was then added and the sample was maintained on ice until ready for use.

Positive control samples containing HIV target DNA were prepared identically to the negative control samples with the exception that 1 $\mu$L of target nucleic acid solution containing $1 \times 10^8$ copies/$\mu$L was added to 1 $\mu$L of salmon sperm stock solution prior to the addition of base.

Several suspensions of the capture and reporter probe reagents were prepared by adding 2-$\mu$L portions of capture probe reagent containing approximately $5 \times 10^6$ capture probe particles (determined on a particle counter) and 1-$\mu$L portions of reporter probe reagent containing approximately $7 \times 10^6$ reporter probe particles and 5-$\mu$L portions of salmon sperm DNA blocking solution to 200-$\mu$L portions of SSC buffer. 2-$\mu$L aliquots of the positive and negative controls were added to each of the above suspensions and these reaction mixtures were placed in a 50° C. water bath. The reaction mixtures were then incubated for time intervals ranging from 0 to 60 min, to monitor the rate of particle aggregation for both negative and positive control samples. Generally 30 min, was sufficient to provide adequate hybridization for detection of test response.

Figure 3A:
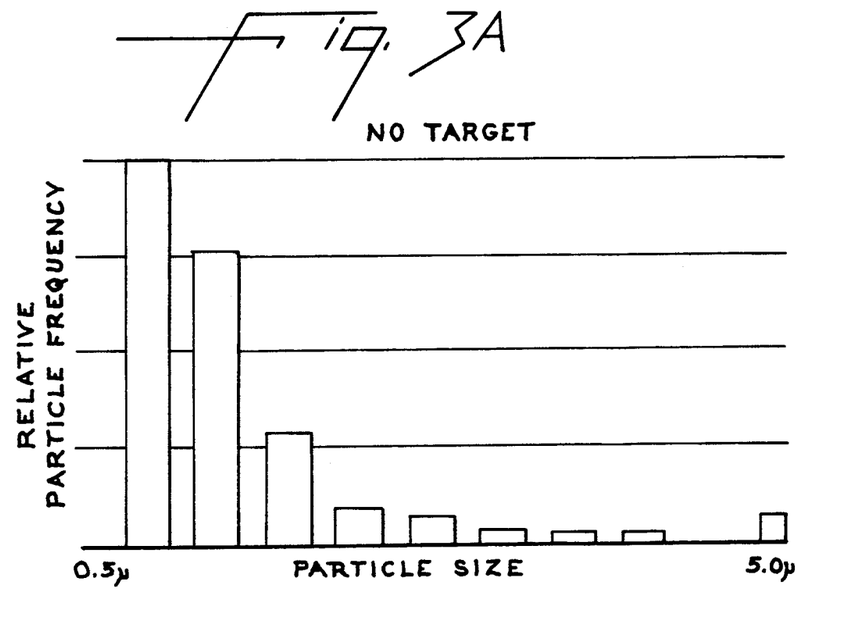
FIGS. 3A and 3B show the particle size distributions for negative control (no target) and positive control (HIV target) samples respectively in the Example.
Figure 3B:
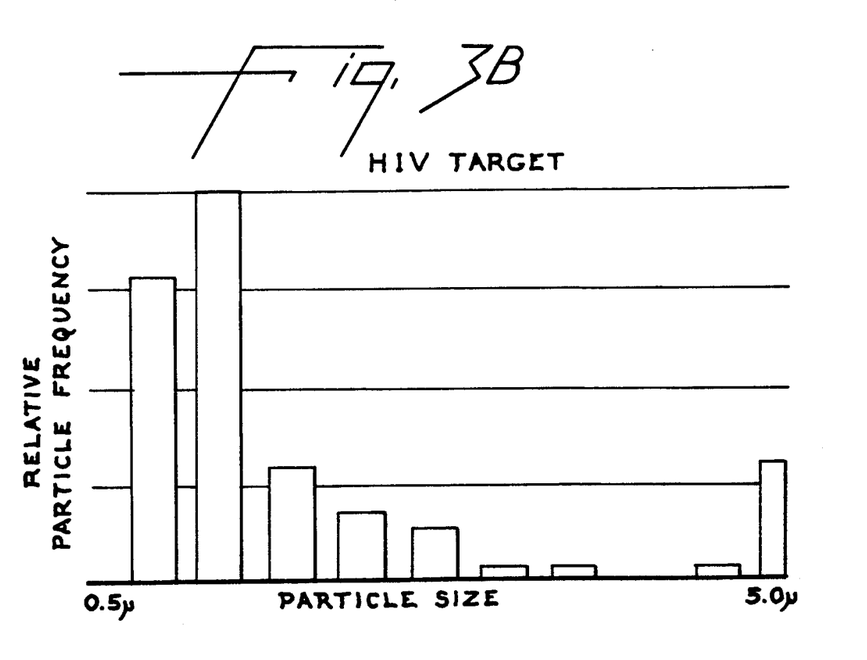

Prior to measurement of the particle size distribution, 20-μL portions of each of these reaction mixtures were diluted into 4 mL of SSC buffer. The diluted reaction mixtures were pumped through the counter at a flow rate of 0.3 mL/min. FIGS. 3A and 3B represent the particle size distributions observed in the absence and presence of target DNA. In the presence of target nuclei acid, the particle size distribution was shifted toward higher particle sizes indicating that particle aggregation detectable by particle counting has occurred.

F. Quantitative Assay for HIV DNA

Control samples were prepared as described in Step E above with the exception that increasing amounts of the stock HIV target DNA were added to control samples prior to the addition of base to obtain a series of samples containing HIV DNA concentrations ranging from $1 \times 10^3 - 2 \times 10^8$ copies of HIV DNA per sample.

As described above, the samples were added to a suspension in tubes containing capture particles, reporter particles, salmon sperm DNA, and SSC buffer. The tubes were placed in an ultrasonic water bath for 10 sec, to mix and then incubated in a 50° C. water bath for 30 min. At this time, 20-μL aliquots of the test mixtures were taken and diluted into 4 mL of SSC buffer to stop the hybridization process.

Figure 4:
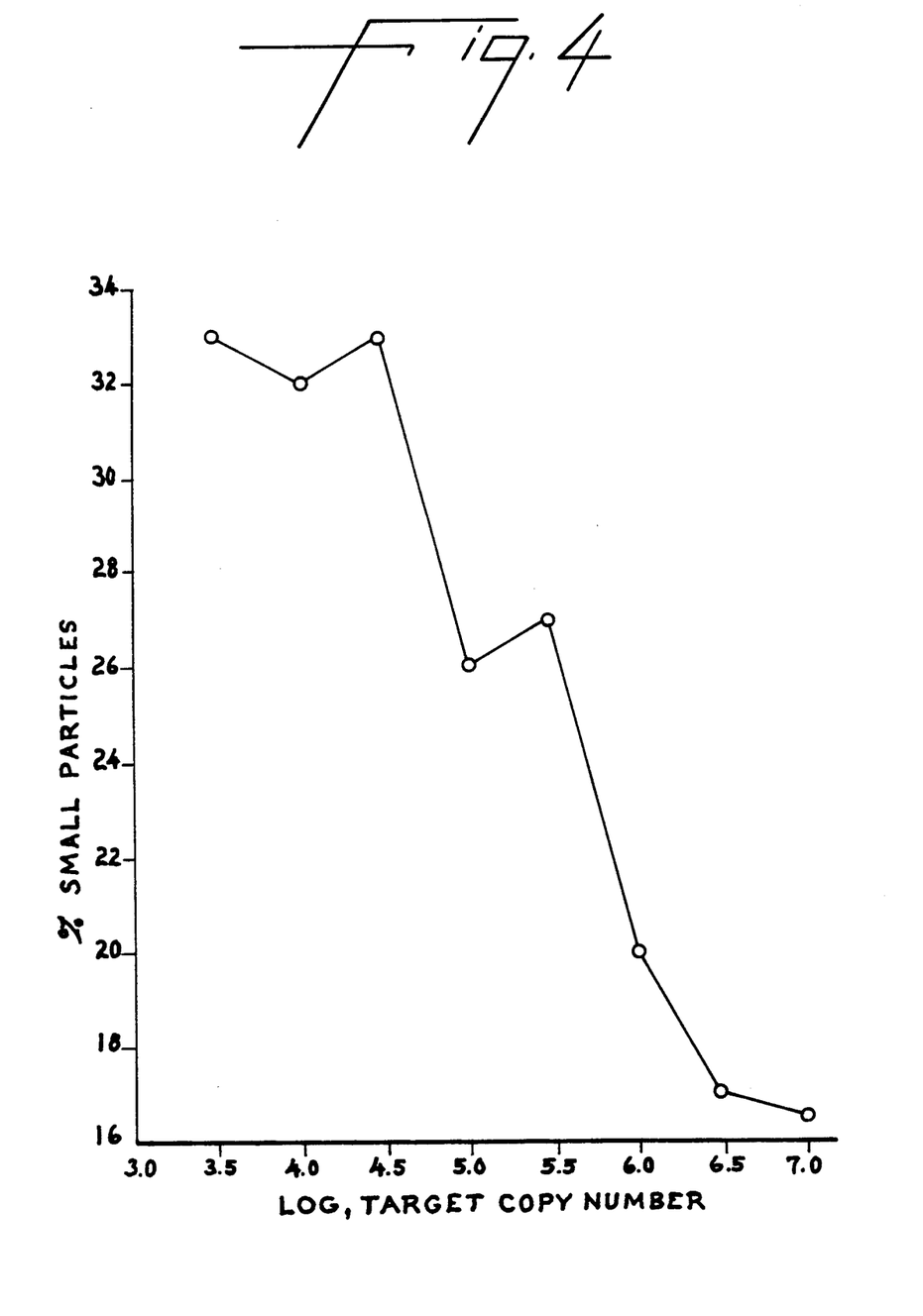
FIG. 4 shows a calibration curve obtained using the assay of the instant invention in the Example.

Particle size measurements were performed as described above. The resulting percentages of small particles (small defined as bands 1 through 5, from left to right, in FIGS. 3A and B) were plotted as a function of target DNA concentration. The results shown in FIG. 4 indicate the lowest level of detectability of between $3 \times 10^4$ and $1 \times 10^5$ copies ($0.2 \times 10^{-18}$ moles).

Quantitative measurements of target DNA in known samples can be carried out by determining the percentage of smaller particles and interpolating the target DNA concentration from dose response curves determined under similar conditions.

What is claimed:

1. A particle counting nucleic acid hybridization assay comprising the steps of:
   (a) contacting a sample suspected of containing target nucleic acid with capture probe and reporter probe wherein
      (i) the capture probe is a particle-bound nucleic acid complementary to and capable of hybridizing with at least a portion of the target nucleic acid and consists essentially of a capture particle having a particle diameter range of 0.01–15 μ and a capture nucleic acid; and
      (ii) the reporter probe consists essentially of a reporter nucleic acid complementary to and capable of hybridizing with at least a portion of the target nucleic acid and a reporter moiety;
   wherein the capture nucleic acid and the reporter nucleic acid are
      (A) complementary to separate portions of the target nucleic acid;
      (B) complementary to distinct portions of the target nucleic acid unless said target nucleic acid contains at least two segments of identical nucleotide sequence of suitable specificity; and
      (C) not complementary to each other;
   (b) determining the presence and/or quantity of target nucleic acid by detecting signals associated with particle aggregation by measuring changes in particle size distribution due to the formation of dimer, trimer, or higher aggregates of the capture and reporter probes with the target nucleic acid in the event the reporter moiety is a particle.

2. A particle counting nucleic acid hybridization assay comprising the steps of:
   (a) contacting a sample suspected of containing target nucleic acid with capture probe and reporter probe wherein
      (i) the capture probe is a particle-bound nucleic acid complementary to and capable of hybridizing with at least a portion of the target nucleic acid and consists essentially of a capture particle having a particle diameter range of 0.01–15 μ and a capture nucleic acid; and
      (ii) the reporter probe consists essentially of a reporter nucleic acid complementary to and capable of hybridizing with at least a portion of the target nucleic acid and a reporter moiety;
   wherein the capture nucleic acid and the reporter nucleic acid are
      (A) complementary to separate portions of the target nucleic acid;
      (B) complementary to distinct portions of the target nucleic acid unless said target nucleic acid contains at least two segments of identical nucleotide sequence of suitable specificity; and
      (C) not complementary to each other;
   (b) determining the presence and/or quantity of target nucleic acid by detecting coincident signals of particle detection and reporter detection in the event the reported moiety is not a particle.

3. The assay of claim 1 or claim 2, wherein both capture and reporter probes contain 18–200 nucleotides.

4. The assay of claim 1 or claim 2, wherein the capture particle is a solid.

5. The assay of claim 4 wherein the solid particle is a shell-core polymer.

6. The assay of claim 1 or claim 2, wherein nucleic acid is linked to capture particle and reporter moiety through heterobifunctional or homobifunctional linking agent.

7. The assay of claim 1 or claim 2, wherein said reporter moiety is selected from the group consisting of fluorescent, absorbent, radioactive, electrical reactance and luminescent moieties and wherein the presence and/or quantity of target nucleic acid is determined by detecting coincident signals of particle and reporter detection.

8. The assay of claim 1, wherein the target nucleic acid is a mixture of target nucleic acids, wherein both capture nucleic acids and reporter nucleic acids are, respectively, complementary to different target nucleic acids in the mixture of target nucleic acids, and wherein the capture particles and reporter particles for each target nucleic acid are of detectably different sizes.

9. The assay of claim 7, wherein the target nucleic acid is a mixture of target nucleic acids, wherein both capture nucleic acids and reporter nucleic acids are, respectively, complementary to different target nucleic acids in the mixture of target nucleic acids, and wherein the coincident signals for each target nucleic acid are detectably different.

10. The assay of claim 9 wherein the reporter moieties for each target nucleic acid are fluorescent and fluoresce at detectably different wavelengths to result in detectably different coincident signals.

11. A particle counting nucleic acid hybridization assay comprising the steps of:

(a) contacting a sample suspected of containing HIV nucleic acid with capture probe and reporter probe wherein
  (i) the capture probe is a particle-bound nucleic acid complementary to and capable of hybridizing with at least a portion of the HIV nucleic acid and consists essentially of a capture particle having a particle diameter range of 0.01–10 μ and a capture nucleic acid; and
  (ii) the reporter probe consists essentially of a reporter nucleic acid complementary to and capable of hybridizing with at least a portion of the target nucleic acid and a reporter particle;
wherein the capture nucleic acid and the reporter nucleic acid are
  (A) complementary to separate portions of the HIV nucleic acid;
  (B) complementary to distinct portions of the HIV nucleic acid; and
  (C) not complementary to each other;
(b) determining the presence and/or quantity of HIV nucleic acid by detecting signals associated with particle aggregation.

* * * * *